United States Patent
Maxa et al.

(10) Patent No.: US 9,145,253 B2
(45) Date of Patent: Sep. 29, 2015

(54) DISPENSING DEVICE WITH PRESSURE RELEASE

(75) Inventors: Steven J. Maxa, Burnsville, MN (US); Adam J. Cernohous, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 38 days.

(21) Appl. No.: 13/387,867

(22) PCT Filed: Jul. 29, 2010

(86) PCT No.: PCT/US2010/043607
§ 371 (c)(1),
(2), (4) Date: Apr. 6, 2012

(87) PCT Pub. No.: WO2011/017181
PCT Pub. Date: Feb. 10, 2011

(65) Prior Publication Data
US 2012/0181300 A1    Jul. 19, 2012

Related U.S. Application Data

(60) Provisional application No. 61/231,122, filed on Aug. 4, 2009.

(51) Int. Cl.
*G01F 11/00*    (2006.01)
*B65D 83/00*    (2006.01)
(Continued)

(52) U.S. Cl.
CPC ............ *B65D 83/0027* (2013.01); *A61C 5/066* (2013.01); *B05C 17/00576* (2013.01);
(Continued)

(58) Field of Classification Search
CPC ............. A61C 5/066; B05C 17/00576; B05C 17/00579; B65D 83/0027; B65D 2205/04; Y10T 29/49826; A61M 2005/3123

USPC ........... 222/386, 386.5, 326, 1, 387; 604/218, 604/311, 222, 221, 89, 90, 93.01, 231; 433/90, 89, 221; 605/92–94, 86 R; 29/428
See application file for complete search history.

(56) References Cited

U.S. PATENT DOCUMENTS 3,967,759 A * 7/1976 Baldwin et al. ............... 222/129
3,998,224 A   12/1976 Chiquiar-Arias
(Continued)

FOREIGN PATENT DOCUMENTS

EP    0 900 599    3/1999
EP    1 738 834    1/2007
(Continued)

OTHER PUBLICATIONS

International Search Report for PCT/US2010/043607 dated Oct. 25, 2010.

*Primary Examiner* — Frederick C Nicolas
*Assistant Examiner* — Bob Zadeh

(57) ABSTRACT

Improved dispensing devices (100) and methods are provided that include a hollow barrel (102) containing the composition to be dispensed along with a piston (120, 220, 320, 420) received in one end (104) of the barrel (102) for dispensing the composition from the opposite end (106) of the barrel (102). At least one tortuous groove (200, 202, 204, 226, 326, 426, 436) extends across the side of the piston (120, 220, 320, 420) and communicates with the exterior of the barrel (102). The groove (200, 202, 204, 226, 326, 426, 426, 436) allows both air and the composition to travel along the side of the piston (120, 220, 320, 420) as the piston advances into the barrel (102). By permitting passage of both air and the composition, the groove (200, 202, 204, 226, 326, 426, 436) eliminates air pockets in the composition while alleviating pressure in the barrel (102) as the piston (120, 220, 320, 420) advances.

18 Claims, 6 Drawing Sheets

(51) Int. Cl.
*A61C 5/06* (2006.01)
*B05C 17/005* (2006.01)
*A61M 5/31* (2006.01)

(52) U.S. Cl.
CPC .. *B05C17/00579* (2013.01); *A61M 2005/3123* (2013.01); *B65D 2205/04* (2013.01); *Y10T 29/49826* (2015.01)

(56) References Cited

U.S. PATENT DOCUMENTS

| | | | |
|---|---|---|---|
| 4,252,118 A | 2/1981 | Richard et al. | |
| 4,492,576 A * | 1/1985 | Dragan | 433/90 |
| 4,572,210 A | 2/1986 | Mckinnon | |
| 4,615,341 A * | 10/1986 | Marzolf et al. | 600/578 |
| 4,632,672 A * | 12/1986 | Kvitrud | 604/222 |
| 4,660,569 A | 4/1987 | Etherington | |
| 4,792,065 A | 12/1988 | Soehnlein et al. | |
| 4,826,483 A | 5/1989 | Molnar, IV | |
| 4,852,772 A * | 8/1989 | Ennis, III | 222/386 |
| 4,869,403 A * | 9/1989 | Bruning | 222/327 |
| 5,178,305 A | 1/1993 | Keller | |
| 5,183,466 A | 2/1993 | Movern | |
| 5,453,093 A | 9/1995 | Haining | |
| 5,459,937 A * | 10/1995 | Albin et al. | 33/479 |
| 5,489,266 A * | 2/1996 | Grimard | 604/89 |
| 5,738,655 A | 4/1998 | Vallelunga et al. | |
| 5,795,337 A * | 8/1998 | Grimard | 604/222 |
| 5,865,798 A * | 2/1999 | Grimard et al. | 604/89 |
| 5,865,803 A * | 2/1999 | Major | 604/122 |
| 5,874,354 A | 2/1999 | Heitzer et al. | |
| 6,095,814 A | 8/2000 | Petrich et al. | |
| 6,572,565 B2 | 6/2003 | Daley et al. | |
| 6,598,766 B1 | 7/2003 | Brugner | |
| 6,632,198 B2 | 10/2003 | Caizza | |
| 6,835,191 B2 * | 12/2004 | Lee et al. | 604/228 |
| 6,899,254 B1 | 5/2005 | Sandholm et al. | |
| 6,916,308 B2 | 7/2005 | Dixon | |
| 7,101,351 B2 | 9/2006 | Crawford et al. | |
| D581,528 S | 11/2008 | Sudo | |
| D583,938 S | 12/2008 | Sudo | |
| 7,503,905 B2 | 3/2009 | Jessop et al. | |
| 7,547,297 B2 | 6/2009 | Brinkhues | |
| 7,677,419 B2 * | 3/2010 | DiGregorio et al. | 222/386 |
| 7,891,528 B2 * | 2/2011 | Costa et al. | 222/386 |
| 2002/0076671 A1 | 6/2002 | Evers et al. | |
| 2002/0077598 A1 | 6/2002 | Yap et al. | |
| 2003/0120220 A1 * | 6/2003 | Lee et al. | 604/240 |
| 2003/0196914 A1 | 10/2003 | Tzou et al. | |
| 2003/0233075 A1 | 12/2003 | Huegli | |
| 2005/0006809 A1 | 1/2005 | Stroppiana | |
| 2005/0137533 A1 | 6/2005 | Sudo et al. | |
| 2006/0178643 A1 * | 8/2006 | Sudo et al. | 604/230 |
| 2007/0078406 A1 | 4/2007 | Lee | |
| 2007/0078407 A1 | 4/2007 | Huang | |
| 2007/0167910 A1 | 7/2007 | Tennican | |
| 2007/0172789 A1 | 7/2007 | Muller et al. | |
| 2007/0250004 A1 | 10/2007 | Tung | |
| 2008/0097387 A1 | 4/2008 | Spector | |
| 2010/0200617 A1 | 8/2010 | Schär | |

FOREIGN PATENT DOCUMENTS

| | | | |
|---|---|---|---|
| EP | 2 221 257 | 8/2010 | |
| GB | 1475430 * | 8/1975 | F16J 1/00 |
| GB | 1 475 430 | 6/1977 | |
| JP | 4 200672 | 7/1992 | |
| WO | WO 01/94028 | 12/2001 | |
| WO | WO 2005/016783 | 2/2005 | |
| WO | WO 2007/047381 | 4/2007 | |
| WO | WO 2007/104037 | 9/2007 | |
| WO | WO 2008/005654 | 1/2008 | |
| WO | WO 2009/029974 | 3/2009 | |

* cited by examiner

DISPENSING DEVICE WITH PRESSURE RELEASE

CROSS REFERENCE TO RELATED APPLICATIONS

This application is a national stage filing under 35 U.S.C. 371 of PCT/US2010/043607, filed Jul. 29, 2010, which claims priority to U.S. Provisional Application No. 61/231,122, filed Aug. 4, 2009, the disclosures of which are incorporated by reference in their entirety herein.

BACKGROUND OF THE INVENTION

1. Field of the Invention

Devices and related methods are provided for dispensing compositions. More particularly, these devices and methods relate to devices using a hollow barrel and a piston received in one end of the barrel to dispense a composition from the opposite end of the barrel. Applications include, but are not limited to, dispensing dental materials such as composites, adhesives, etchants, glass ionomers, cements, and sealants.

2. Description of the Related Art

Positive displacement dispensers, including syringes and capsules, are used in diverse industrial and commercial applications. Such devices find uses in medicine, laboratory processes, cooking, adhesives, inks, and others. Particular applications of devices are found in, for example, dispensing and measuring quantities of medications, adhesives, lubricants, resins, or even food products such as cake frosting.

One common type of positive displacement dispenser is a syringe. Syringes use a simple piston pump consisting of a plunger that fits tightly in a cylindrical tube or barrel. A composition is provided in a chamber within the barrel, and the plunger can be pulled and pushed along the barrel, allowing the syringe to take in and/or expel the composition through an orifice located at an open end of the barrel. Optionally, the open end is fitted with a hypodermic needle, nozzle, or tubing to help direct the flow of the composition into and out of the barrel.

In many of applications, it is desirable for air pockets or air bubbles to be expelled from the chamber of the syringe to prevent air from becoming entrained in the dispensed composition. In some cases, this can be accomplished by merely inverting the syringe to consolidate air bubbles at the front end of the chamber and discharging them through the orifice prior to use. However, this is an inconvenient extra step and not always practical or possible when dealing with viscous pastes or liquids.

Another approach to this problem is to use vented syringes. Vented syringes generally employ a plunger with an exit channel that is impervious to the composition but readily allows the passage of air. As the plunger is advanced into the barrel of the syringe, the channel redirects undesirable air pockets or bubbles out of the chamber to eliminate them from the dispensed composition. Examples of vented syringe concepts have been disclosed in issued U.S. Pat. Nos. 4,572,210 (McKinnon), 4,660,569 (Etherington), 5,865,803 (Major), 6,916,308 (Dixon), and 7,503,905 (Jessop et al.), U.S. Patent Publication No. 2002/0076671 (Markus et al.), published British Patent Application No. GB 1 475 430 (Fischbach), and International Application No. WO 2009/029974 (Kiehne).

SUMMARY OF THE INVENTION

Provided are improved dispensing devices and related methods for dispensing composition with a high degree of precision and a consistent flow rate. This outcome can be achieved by using a hollow barrel containing the composition to be dispensed along with a piston for urging the composition through an exit opening on the barrel. One or more tortuous grooves are located along the sides of the piston, allowing both air and the composition to travel along the sides of the piston as the piston advances into the barrel. By permitting passage of both air and the composition, the groove eliminates air pockets in and around the composition while simultaneously preventing an undue increase in internal pressure as the piston advances into the barrel. This in turn dramatically reduces residual discharge of the composition, also known as "run-on" or "drool", thereby providing superior control in dispensing the composition.

This configuration is particularly advantageous when dispensing viscous compositions that are thixotropic or undergo shear-thinning. Both of these types of compositions can dramatically decrease in viscosity when subjected to shear stress. As a result, these compositions behave unpredictably in conventional vented syringes. Under high shear rates, they either leak out through the venting channels or clog the vents and prevent proper expulsion of air from the composition. The provided dispensing device overcomes this problem by conveying both air and the composition along sized grooves having a sufficiently long flow path such that leakage does not occur. Additionally, the provided dispensing device does not rely on moving parts in order to vent air from the interior of the barrel. This enables a solid-state piston construction having superior robustness and performance compared to piston configurations that use moving parts.

In one aspect, the present invention is directed to a device for dispensing a composition comprising a hollow barrel including an inner surface, open front end and an open back end, a piston having shape complemental to the inner surface and received in the back end of the barrel to present a chamber located between the piston, the inner surface and the front end of the barrel, and a tortuous groove extending across the piston, wherein the groove communicates with both the chamber and the back end of the barrel when there is zero pressure differential between the chamber and the back end of the barrel and further wherein the groove is sized to allow the composition to travel along the groove as the composition is being dispensed.

In another aspect, the invention is directed to a method of assembling a dispensing device comprising providing a hollow barrel having two open ends and at least partially filled with a composition, inserting a piston into one end of the barrel, wherein at least one tortuous groove extends across the piston to vent air pockets in and around the composition as the piston is inserted, and advancing the piston further into the barrel to urge some of the composition toward the opposite end of the barrel while simultaneously urging some of the composition into and along the groove, wherein the groove maintains open communication between the composition and the one end as the piston traverses the barrel.

In still another aspect, the invention is directed to a method of dispensing a composition comprising providing a hollow barrel having two open ends and at least partially filled with the composition, providing a piston received in one end of the barrel, wherein at least one tortuous groove extends across the piston, and advancing the piston into the barrel to dispense the composition from the opposite end of the barrel while simultaneously urging the composition along the groove, wherein the groove maintains open communication between the composition and the one end as the piston traverses the barrel.

These and other aspects of the invention are described in more detail in the paragraphs that follow and are illustrated in the accompanying drawings.

BRIEF DESCRIPTION OF THE DRAWINGS

FIG. 6b is an inset showing in greater detail the grooves located on the piston of FIG. 6a.

DEFINITIONS

As used herein:

"Composition" refers to a deformable liquid or paste to be dispensed by a device or method of the present invention;

"Thixotropic" refers to a composition that decreases in viscosity over time at a constant shear rate;

"Shear-thinning" refers to a composition that decreases in viscosity with increasing shear rate;

"Tortuous" means along a path that includes a plurality of twists, bends, or curves;

"Helical" means along a generally spiral-shaped path;

"Coincident" means travelling in a synchronized fashion;

"Zigzag" means along a path that includes a series of short sharp turns or angles;

"Serpentine" means along a path that curves in alternate directions; and

"Circumference" means the distance along a closed path measured around the periphery of an object.

DETAILED DESCRIPTION OF THE PREFERRED EMBODIMENTS

Figure 1:
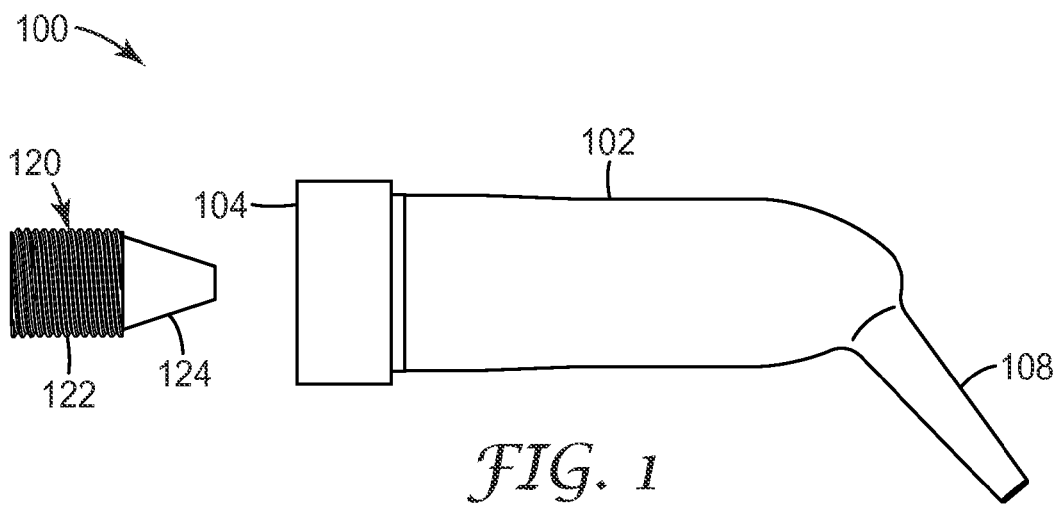
FIG. 1 is an exploded elevational view of a device according to one embodiment of the present invention.
Figure 2:
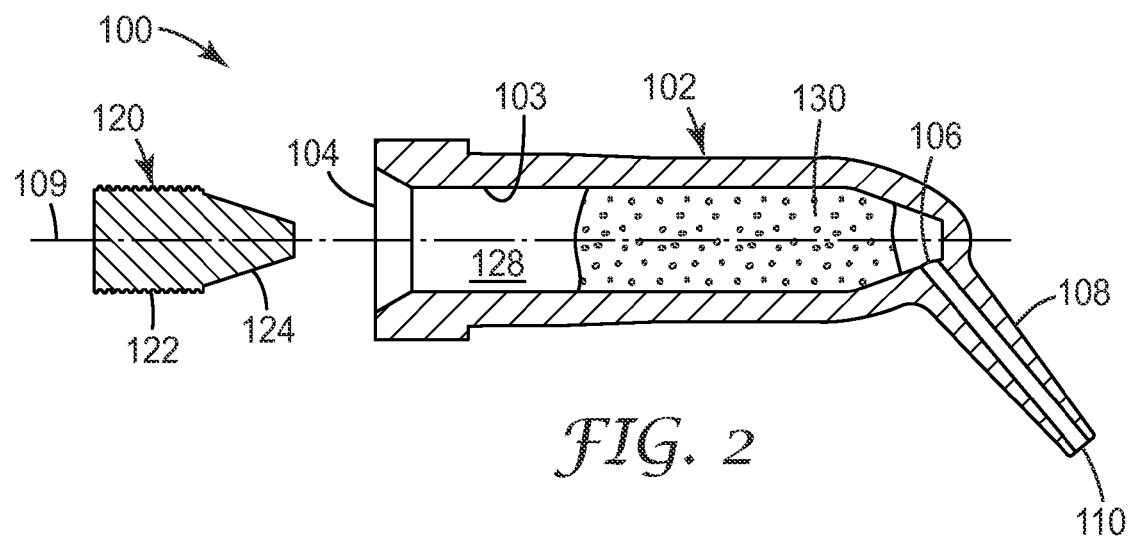
FIG. 2 is an exploded cross-sectional view of the device of FIG. 1.

FIG. 1 shows an elevational exploded view of a dispensing device illustrating one exemplary embodiment of the invention and broadly designated by the numeral 100. FIG. 2 shows an exploded cross-sectional view of the same. As shown, dispensing device 100 includes an elongated hollow barrel 102 having an inner surface 103, an open back end 104 and an open front end 106. As shown, the barrel 102 has a circular cross-section, although it may alternatively have a cross-section that is generally square, rectangular, elliptical, or some other shape. Optionally and as shown, a tapered nozzle 108 extends outwardly from barrel 102, providing a narrow exit hole 110 in communication with the open front end 106. In the figures, the nozzle 108 extends at approximately a 45 degree angle from the longitudinal axis 109 of the barrel 102 to facilitate dispensing, but other relative orientations are also possible.

The open back end 104 of the barrel 102 receives a piston 120. The piston 120 has a generally cylindrical body 122, along with a conical tip 124 connected to the body 122 and extending outwardly into the barrel 102. Optionally and as shown in FIGS. 1-2, the conical tip 124 has the shape of a truncated cone. Preferably, the shape of the cylindrical body 122 is complemental to the inner surface 103 such that advancing the piston 120 into the barrel 102 provides an interference fit. The barrel 102 also includes a chamber 128. When the dispensing device 100 is assembled, the chamber 128 is located between the piston 120, the inner surface 103, and the front end 106.

As shown in FIG. 2, a composition 130 resides in the chamber 128 and at least partially fills the barrel 102. The composition 130 may be a paste, gel, viscous liquid, or any other deformable material capable of being displaced and extruded out of the dispensing device 100. In exemplary embodiments, the composition 130 is a dental material such as a composite, adhesive, etchant, glass ionomer, cement, or sealant.

The barrel 102 and piston 120 can be manufactured by machining, extrusion, injection molding, or other casting process from one or more suitable polymers. Examples of suitable polymers include, but are not limited to, polypropylene, polypropylene copolymer, polyethylene, polyethylene copolymer, cyclo-olefin-copolymer, acrylonitrile-based copolymer, polyvinyl chloride, polyvinylidene chloride and polyamide. Blends and laminates of these polymers are also possible. Advantageously, the barrel 102 could be made from a translucent material so that the amount of the composition 130 may be visibly determined through the walls of the dispensing device 100. In the event that the barrel 102 is translucent, the piston 120 may be manufactured from a dark-colored polymer to allow the position of the piston 120 in the barrel 102 to be easily visualized.

As another option, the barrel 102, piston 120, or both may be made from an opaque light-blocking material. Use of such materials can extend the shelf life of the composition 130, especially when the composition 130 is a photosensitive composition such as a light curable dental composite, primer or adhesive. In some embodiments, the barrel 102 and piston 120 are made light blocking by using polymers filled with carbon black or metallic particles such as disclosed in pending U.S. Patent Publication No. 2003/0196914 (Brennan et al.).

Further structural details of the piston 120 are provided by reference to FIGS. 3, 4, 5, 6a, and 6b, which show the piston 120 in perspective view, elevational view, top view, and cross-sectional views, respectively.

Figure 3:
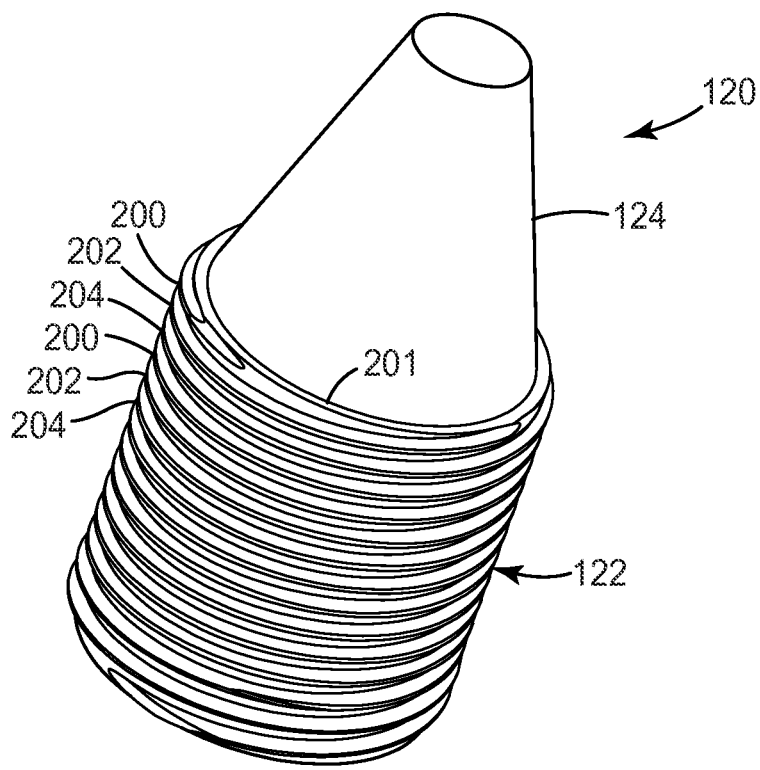
FIG. 3 is a perspective view of a piston used in the device of FIGS. 1 and 2.
Figure 4:
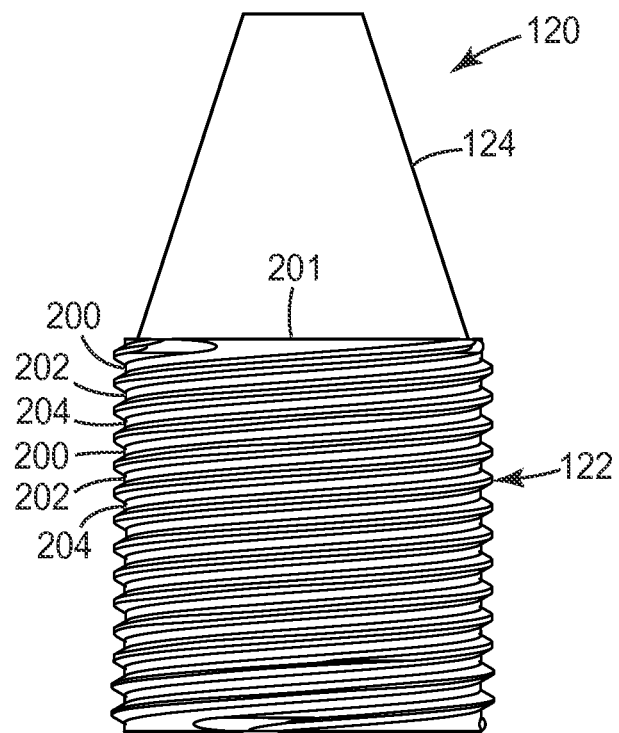
FIG. 4 is an elevational side view of the piston in FIG. 3.

As shown in FIGS. 3 and 4, three tortuous grooves 200, 202, 204 extend across the cylindrical body 122 of the piston 120. The grooves 200, 202, 204 are parallel and coincident with each other and form a helix around the cylindrical body 122 about the longitudinal axis of the piston 120. Using a helical configuration is advantageous, since it is easy to manufacture and allows the grooves 200, 202, 204 to traverse significant distances even when the surface area of the body 122 is limited. In some embodiments, the helical grooves 200, 202, 204 have a pitch ranging from 4 to 40 turns per centimeter (approximately 10 to 100 turns per inch).

While one type of helical groove is shown here, other helical configurations are also possible. For example, greater or fewer grooves may be used. As another example, the grooves 200, 202, 204 may coil in either a clockwise or counterclockwise direction. As still another example, grooves having intermittent step bends may be used instead of the smooth continuous grooves shown.

When the piston 120 is received in the barrel 102, each of the grooves 200,202,204 extends along the inner surface 103 and communicates with both the chamber 128 and the back end 104 of the barrel 102. Advantageously, the grooves 200, 202,204 communicate with both the chamber 128 and the back end 104 of the barrel 102 even when there is zero pressure differential between the chamber 128 and the back end 104 of the barrel 102. Preferably, the piston 120 maintains a generally rigid shape and does not deflect or deform in response to a pressure differential between the inside and outside of the barrel. Advantageously, the grooves 200,202, 204 allow the pressure differential between the inside and outside the barrel 102 to be minimized.

Figure 5:
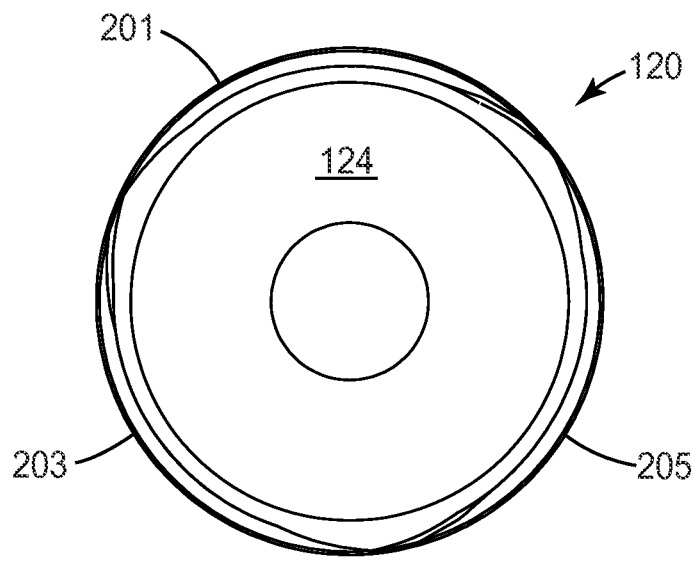
FIG. 5 is a top view of the piston in FIGS. 3 and 4.

In more detail, the grooves 200,202,204 communicate with the chamber 128 at respective start points 201,203,205. As shown in FIG. 5, the start points 201,203,205 are located along the edge between the cylindrical body 122 and the conical tip 124 of the piston 120. Preferably and as shown in FIG. 4, the start points 201,203,205 are evenly spaced apart from each other along the inner surface 103 to provide multiple locations where the contents of the chamber 128 can be vented. The grooves 200,202,204 terminate at respective end points on the opposite end of the piston 120, where they lead out of the back end 104 of the barrel 102 into the ambient environment.

Figure 6A:
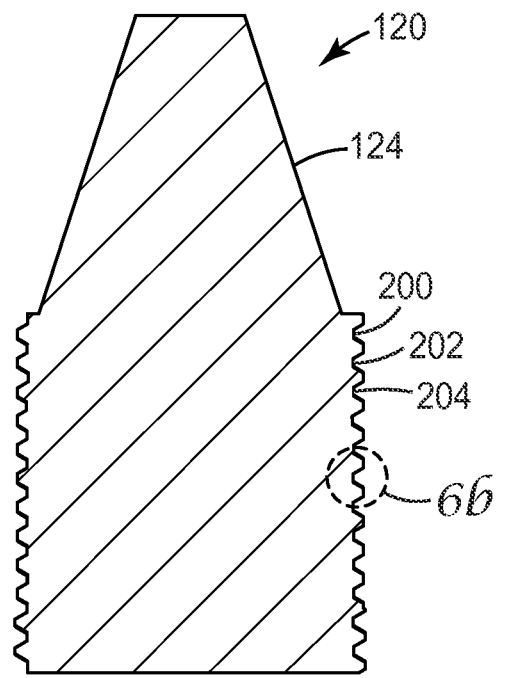
FIG. 6a is a lengthwise cross-sectional view of the piston in FIGS. 3-5.
Figure 6B:
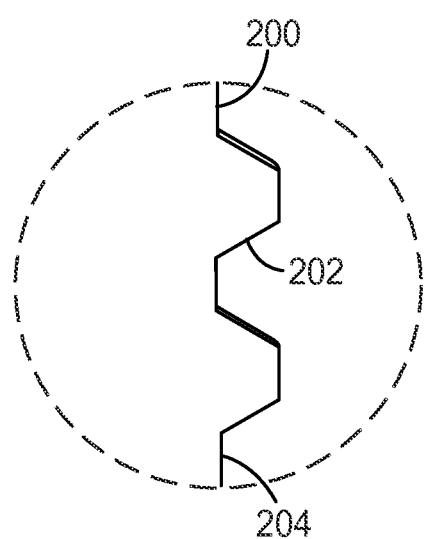

FIGS. 6a and 6b show the piston 120 in a lengthwise cross-sectional view. As shown in the inset, the grooves 200, 202,204 have a generally trapezoidal cross-section. Semicircular grooves, V-shaped grooves, rectangular grooves, or grooves of any other shape may also be used.

The dispensing device 100 can be assembled by a manufacturer or an end user as follows. First, the composition 130 is either manually or automatically loaded into the back end 104 of the barrel 102 to form a plug as shown in FIG. 2. Then, the piston 120 is inserted into the back end 104 in the orientation shown in FIG. 2 to form a tight seal between the grooved areas of the body 120 and the inner surface 103 of the barrel 102.

Upon urging the piston 120 deeper into the barrel 102, the grooves 200,202,204 vent air pockets in and around the composition 130 out of the chamber 128. In this step, the conical tip 124 is advantageous in that it penetrates into the plug of composition 130 and directs air pockets or air bubbles toward the start points 201,203,205 where they are evacuated through the grooves 200,202,204 and out of the device 100. Preferably, the piston 120 maintains a rigid shape and does not deflect or deform once received in the barrel 102.

Implementing a piston 120 that maintains a rigid shape while sliding through the barrel 102 is especially advantageous because it provides a static venting mechanism. Static venting mechanisms are generally easier to manufacture and more robust than devices that rely on moving parts, such as moving flaps, folds, or membranes. As particularly indicated by groove exit points 126 in FIG. 7, the piston 120 does not, at any time, form a seal between the front end 106 and the back end 104 of the barrel 102. This configuration allows the grooves to maintain open communication between the composition 130 and the back end 104 as the piston 120 traverses the barrel 102.

Once all or nearly all of the remaining air bubbles have been removed, the piston 120 is advanced further into the barrel 102. This urges some of the composition 130 toward the open front end 106 and into the nozzle 108 while simultaneously urging some of the composition 130 into and along one or more of the grooves 200,202,204. By providing an alternative path for the composition 130 to escape, the grooves 200,202,204 alleviate pressure in the chamber 128 without the need to dispense composition 130 from the nozzle 108. The dispensing device 100 is now ready for use. If the device 100 is to be stored in this state, the nozzle 108 can optionally be sealed or capped to prevent contamination.

When it is desired to dispense the composition 130, the piston 120 is simply advanced into the barrel 102 with the mechanical assistance of a hand held dispensing device such as disclosed in issued U.S. Pat. No. 6,095,814 (Petrich et al.) or U.S. Patent publication No. 2007/0172789 (Muller et al.). As the piston 120 advances, the composition 130 is extruded through the nozzle 108 and out of the exit hole 110. The advancement of the piston 120 also urges the composition 130 along one or more of the grooves 200,202,204. Advantageously, the grooves 200,202,204 are sized to allow the composition 130 to travel along the grooves 200,202,204 at the same time it is being dispensed from the nozzle 108.

Figure 7:
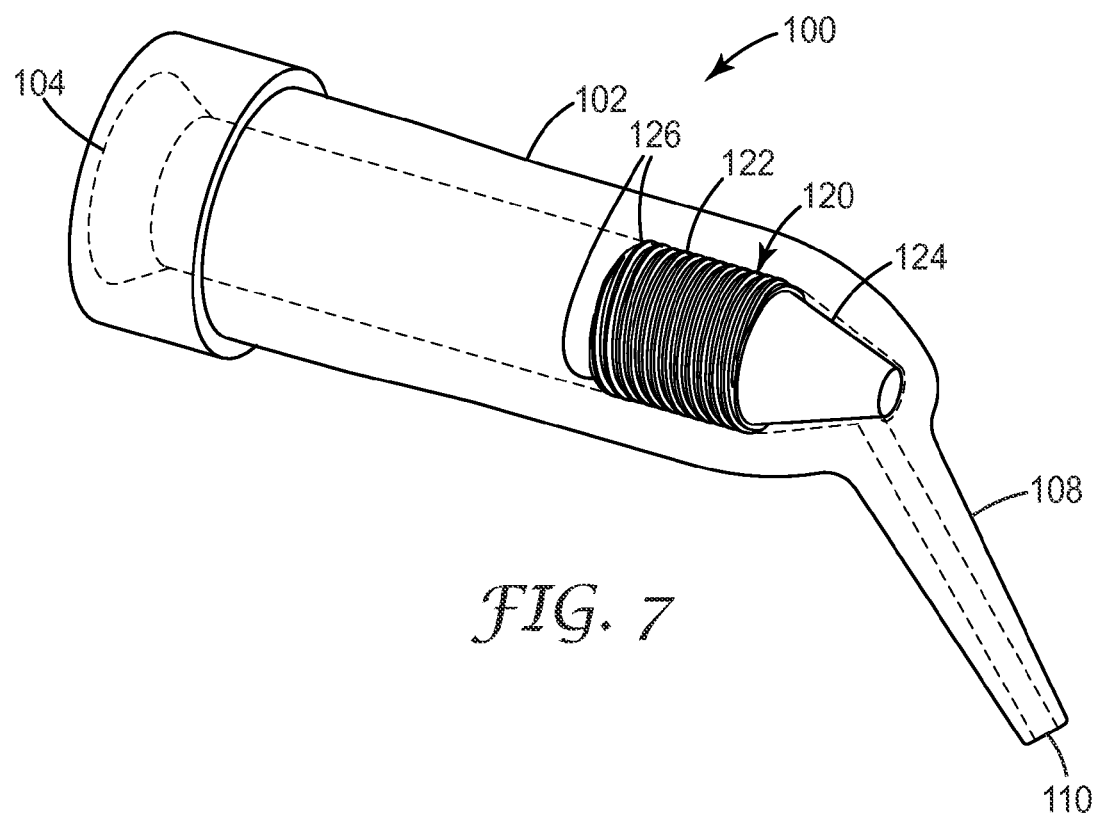
FIG. 7 is a perspective view of the device of FIGS. 1 and 2 with the piston fully advanced into the barrel.

Preferably the grooves 200,202,204 are sized such that the composition only travels along a portion of the full length of the grooves 200,202,204 when the piston 120 is fully advanced into the barrel 102 as shown in FIG. 7. In some embodiments, the grooves 200,202,204 have a length-to-width aspect ratio of at least 50:1. That is, the overall length of each groove 200,202,204 is at least 50 times greater than the width of the groove 200,202,204 (the width being defined tangent to the surface of the cylindrical body 122 and perpendicular to the longitudinal axis of the groove 200,202,204). In other embodiments, the grooves 200,202,204 have a length-to-width aspect ratio of at least 75:1. In other embodiments, the grooves 200,202,204 have a length-to-width aspect ratio of at least 100:1.

It is preferable that the grooves 200,202,204 provide a sufficiently long flow path with respect to the dimensions of barrel 102 to prevent undesirable leakage of the composition 130 out of the dispensing device 100. In some embodiments, each of the tortuous grooves 200,202,204 has a length at least 5 times, at least 10 times, or at least 20 times the diameter of the inner surface 103 of the barrel 102 (also equivalent to the outer diameter of the cylindrical body 122).

It is also preferable that the grooves 200,202,204 have sufficient width and/or depth to allow the composition 130 to easily flow into and along the grooves 200,202,204 without the application of excessive force on the piston 120. These dimensions depend in part on the nature of the composition 130. A composition 130 with a very low viscosity, for example, should be paired with grooves 200,202,204 with a relatively small cross-section. On the other hand, a composition 130 with a high viscosity should be paired with grooves 200,202,204 having a relatively large cross-section. In exemplary embodiments, each of the grooves 200,202,204 has a cross-sectional area ranging from 0.006 square millimeters to 0.06 square millimeters, defined in a plane perpendicular to the longitudinal axis of the groove 200,202,204.

The use of tortuous grooves 200,202,204 provides several significant enhancements in the operation of the dispensing device 100. First, this method leads to a consistent flow rate and superior control in dispensing precise quantities of the composition 130. Second, the grooves 200,202,204 prevent undesirable "run on" or "drool" of the composition 130 out of the nozzle 108 when advancement of the piston 120 into the barrel 102 is stopped. Third, the tortuous nature of the grooves 200,202,204 allows residual air bubbles to be continually evacuated from the chamber 128 while avoiding leakage of the composition 130 from the back end 104 of the barrel 102. The device 100 performs unexpectedly well in particular with thixotropic or shear-thinning compositions, which decrease in viscosity under shear and tend to leak out of conventional vented dispensing devices.

Figure 8:
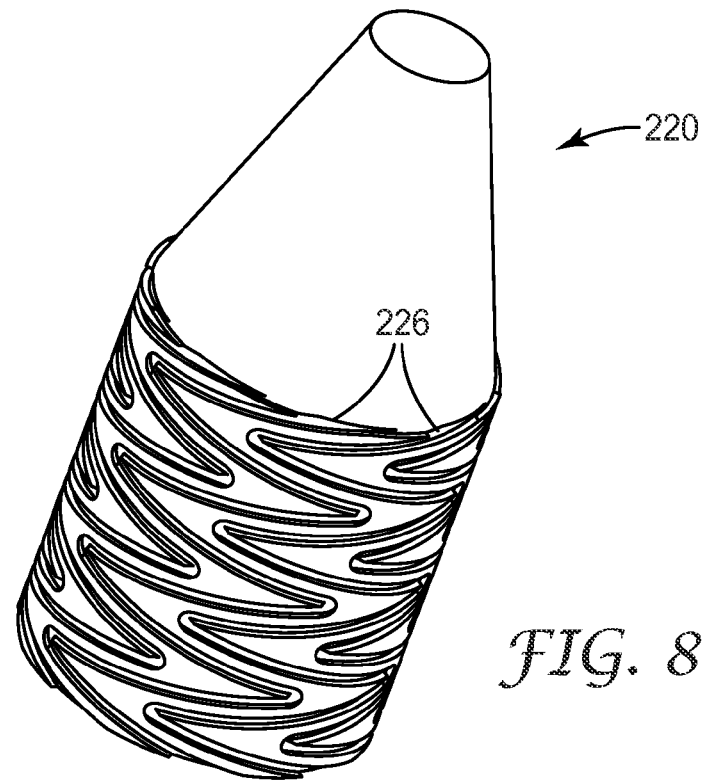
FIG. 8 is a perspective view of a piston according to another embodiment of the invention.
Figure 9:
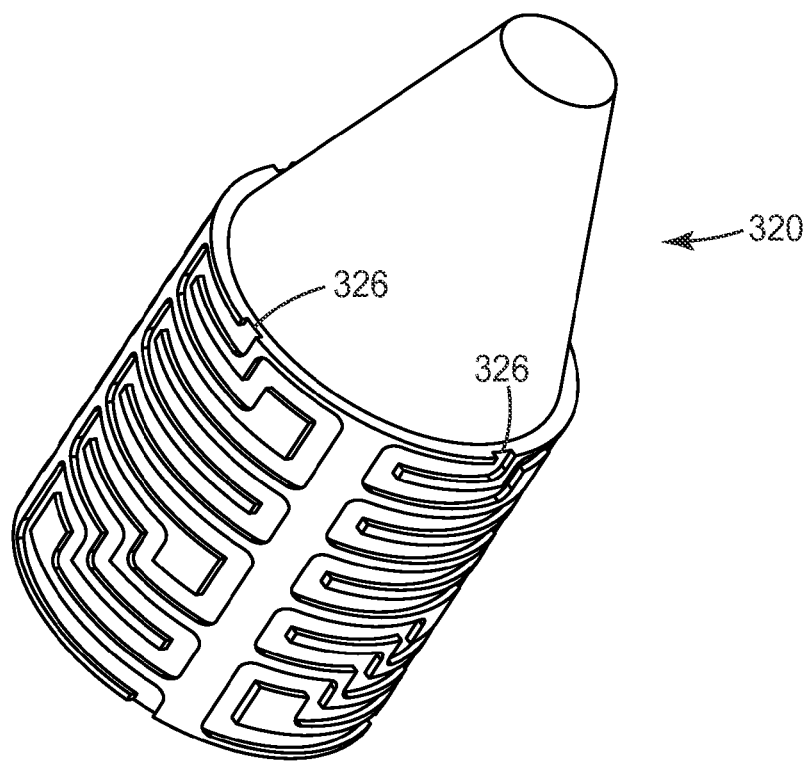
FIG. 9 is a perspective view of a piston according to still another embodiment of the invention.

FIGS. 8 and 9 show alternative embodiments with respect to the piston 120. For example, FIG. 8 shows a piston 220 similar in some respects to the piston 120, except eight tortuous grooves 226 extend across the piston 220 in a generally zigzag configuration. As another example, FIG. 9 shows a piston 320 according to another embodiment of the invention where four tortuous grooves 326 extend across the piston 320 in a generally serpentine configuration. Other configurations are also possible in view of the considerations identified above, including the length-to-width aspect ratio, length-to-diameter ratio, and cross-sectional area of the groove(s).

Figure 10:
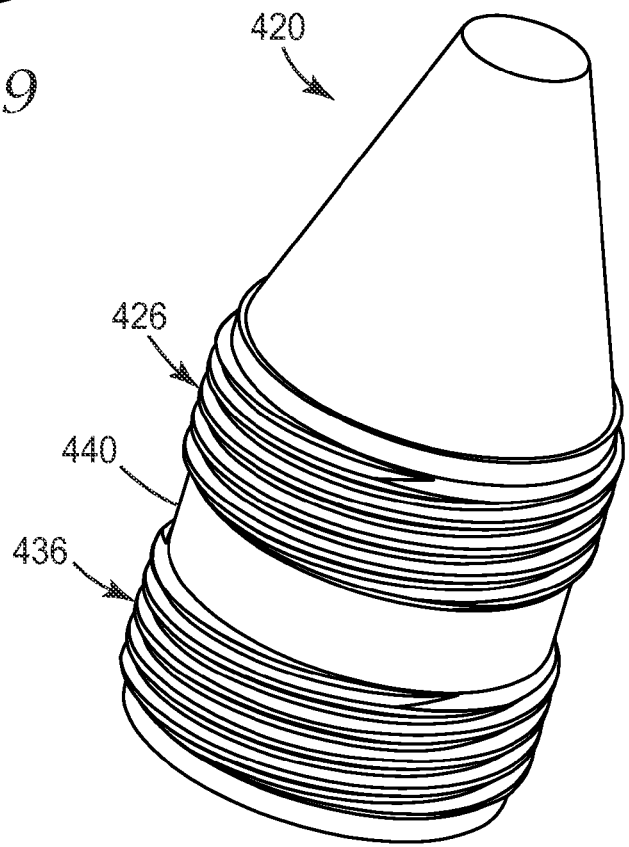
FIG. 10 is a perspective view of a piston according to yet another embodiment of the invention.

FIG. 10 shows still another alternative piston embodiment. Piston 420 has an overall shape that is similar to that of the piston 120. However, unlike the piston 120, two separate and distinct grooved regions 426,436 extend across the cylindrical body of the piston 420, where each region 426,436 includes a plurality of grooves similar to the grooves 200,202, 204 presented in FIGS. 3-6. As shown in FIG. 10, the grooved regions 426,436 are spaced apart from each other in directions parallel to the longitudinal axis of the cylindrical body. Additionally, the cylindrical body of the piston 420 between the grooved regions 426,436 has a reduced diameter as shown in FIG. 10. Thus, when the piston 420 is received in a barrel (such as, for example, barrel 102), an annular cavity 440 is formed between the cylindrical body of the piston 420 and the inner surface of the barrel and extends between the grooved regions 426,436.

The annular cavity 440 advantageously reduces the contact area with the surrounding structure and facilitates sliding between the piston 420 and the barrel. Reduction of the contact area is particularly useful when these components are interference fit with each other, since excessive friction between the grooved regions 426,436 of the piston 420 and the barrel can be problematic. While a single grooved region having the same area might also afford this benefit, separating the grooves into two grooved regions 426,436 located on opposite ends of the piston 420 facilitates alignment of the piston 420 during insertion into the barrel. The grooved regions 426,436 further prevent jamming or binding of the piston 420 as it slides through the barrel. Optionally, three or more grooved regions could be used.

Aspects of this invention are further illustrated by the following examples:

EXAMPLES

Example 1

Pistons Made by Injection Molding

A polypropylene piston (provided by Scientific Plastics Corporation in North St. Paul, Minn.) was made by injecting a molten black polypropylene resin at approximately 232 degrees Celsius (450 degrees Fahrenheit) into a specially machined tool steel mold. The piston had an overall length of 0.762 centimeters (0.300 inches) and an outside diameter of 0.409 centimeters (0.161 inches). The piston consisted of two contiguous sections. One was cylindrical and extended across approximately half of the piston length. The other section tapered, in a conical fashion, to a flattened end. Two grooved sections were located on the cylindrical portion of the piston. Each grooved section consisted of a multi-start set of 3 grooves and formed a circumferential band around the body of the piston, with a width of about 0.140 centimeters (0.055 inches). The grooved sections were separated by a coaxial annular cavity with a width of about 0.116 centimeters (0.046 inches). The V-shaped grooves had a pitch of 12 turns per centimeter (30 turns per inch) and a cross-sectional area of 0.019 square millimeters (0.00003 square inches).

Figure 11:
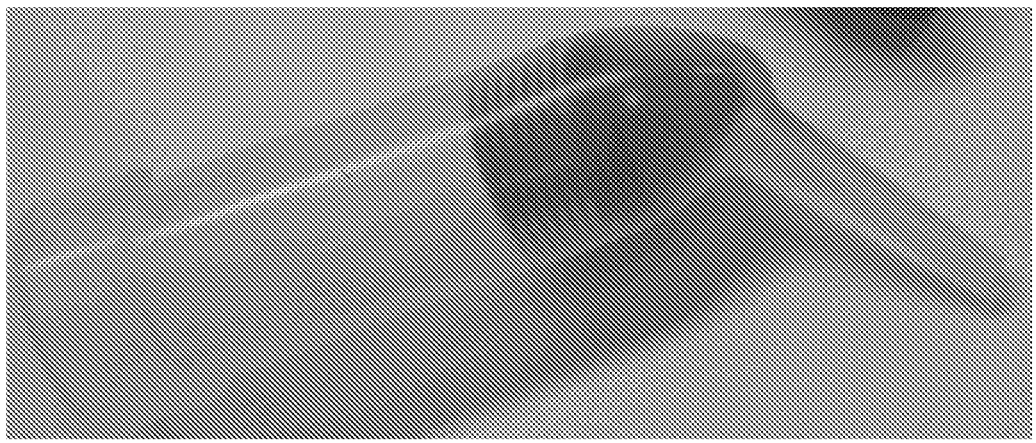
FIG. 11 is an elevational side view of a device prototype manufactured according to FIGS. 1 and 2.

A hollow cylindrical syringe barrel was injection molded from an unpigmented polypropylene resin using a method similar to that described above. The barrel had an open back end and an open front end, the front end tapering to a nozzle, or dispensing tip. The inside diameter of the barrel was 0.401 centimeters (0.158 inches) and the length of the barrel was 1.59 centimeters (0.625 inches). The inside diameter of the barrel was slightly less than the outside diameter of the piston, thereby creating an interference fit. The piston and barrel are shown assembled in FIG. 11.

Example 2

Extrusion of a Flowable Composite Dental Material

The barrel from Example 1 was partially filled with FILTEK brand Supreme Plus Flowable Restorative (available from 3M Company, St. Paul, Minn.). The composite had an approximate viscosity of 2000 Pascal-seconds, although it exhibited shear thinning during use. The piston from Example 1 was inserted into the barrel and pressed into the composite with the mechanical assistance of a handheld dispensing gun (part no. 5706SD, available from 3M Company in St. Paul, Minn.). As the trigger of the dispensing gun was depressed, air pockets in the barrel were expelled through the grooves. Once the air was fully expelled, composite material began to flow from the dispensing tip. The composite paste traveled about 1.5 turns, or 1.9 centimeters (0.75 inches) into the grooves at full advancement of the piston into the barrel. No leakage from the rear of the grooves was observed.

Example 3

Extrusion of a Composite Restorative Dental Material

The barrel from Example 1 was partially filled with FILTEK brand Supreme Plus Universal Restorative (available from 3M Company, St. Paul, Minn.), a composite having a paste-like viscosity. The piston from Example 1 was inserted into the barrel and pressed into the composite to extrude the composite from the dispensing tip. Air was expelled through the grooves, and, once the air was expelled, the composite material began to extrude from the dispensing tip. No leakage from the rear of the grooves was observed at full advancement of the piston into the barrel.

Example 4

Extrusion of a Sealant Dental Material

A barrel from Example 1 was partially filled with CLINPRO brand Sealant (available from 3M Company, St. Paul, Minn.). This sealant was considerably less viscous than the materials tested in Examples 2 and 3, with a viscosity in the range of 1.2 to 3.4 Pascal-seconds. The piston from Example 1 was inserted into the barrel and pressed into the sealant to extrude the composite from the dispensing tip. Air was expelled through the grooves, and, once the air was expelled, the sealant material began to extrude from the dispensing tip.

The sealant traveled about 1.5 turns, or 1.9 centimeters (0.75 inches) into the grooves at full advancement of the piston into the barrel.

Example 5

Extrusion of a Flowable Composite Dental Material

This example was similar to Example 2 above but used a piston having grooves with larger cross-sectional area. While the piston in this example had a similar overall shape and size to that of Example 2, the grooves had a cross-sectional area of 0.053 square millimeters (0.000082 square inches) and a pitch of 7.9 turns per centimeter (20 turns per inch). Also, unlike the piston in Example 2, this piston was manufactured from a 3D digital model using a PERFACTORY brand SXGA+ rapid prototyping system available from EnvisionTEC GmbH (Gladbeck, GERMANY). The resin used for this part was a PERFACTORY brand R11 liquid photopolymer, also available from EnvisionTEC GmbH. Subsequent to the 3D printing process, the piston underwent a post-UV curing step as well as the removal of some support structures to provide the finished product.

As before, the barrel from Example 1 was partially filled with FILTEK brand Supreme Plus Flowable Restorative. The piston was then inserted into the barrel and pressed into the composite to extrude the composite from the dispensing tip. Air was expelled through the grooves by advancing the piston. Once the air was expelled, the composite material began to extrude from the dispensing tip. The composite material traveled about 3.2 turns, or 4.1 centimeters (1.6 inches) into the grooves. There was no leakage from the rear of the grooves at full advancement of the piston into the barrel. In this case, however, the composite material had traveled nearly the full distance through the grooves.

All of the patents and patent applications mentioned above are hereby expressly incorporated by reference. The embodiments described above are illustrative of the present invention and other constructions are also possible. For example, the piston and barrel embodiments shown herein may be generally extended to any and all capsule or syringe devices within the capabilities of one of ordinary skill in the art. Accordingly, the present invention should not be deemed limited to the embodiments described in detail above and shown in the accompanying drawings, but instead only by a fair scope of the claims that follow along with their equivalents.

What is claimed is:

1. A device for dispensing a composition comprising:
a hollow barrel including an inner surface, open front end and an open back end;
a piston having shape complemental to the inner surface and received in the back end of the barrel to present a chamber located between the piston, the inner surface and the front end of the barrel, wherein the piston comprises a cylindrical body having a surface;
two or more grooved regions, each of the two or more grooved regions having a tortuous groove located on the surface of the cylindrical body of the piston and extending along the inner surface of the barrel, where the two or more grooved regions are spaced apart from each other in directions parallel to a longitudinal axis of the cylindrical body to form an annular cavity between the cylindrical body of the piston and the inner surface of the barrel that extends between the two or more grooved regions, wherein the tortuous groove of each of the two or more grooved regions communicates with both the chamber and the back end of the barrel when there is zero pressure differential between the chamber and the back end of the barrel and further wherein the tortuous groove of each of the two or more grooved regions is sized to allow the composition to travel along the tortuous groove as the composition is being dispensed; and one or more additional tortuous grooves adjacent the tortuous groove of each of the two or more grooved regions to form a plurality of grooves that are parallel and coincident with each other.

2. The device of claim 1, wherein the tortuous groove has a length-to-width aspect ratio of at least 50:1.

3. The device of claim 1, wherein the tortuous groove has a length-to-width aspect ratio of at least 100:1.

4. The device of claim 1, wherein the tortuous groove assumes a generally zigzag configuration.

5. The device of claim 1, wherein the tortuous groove assumes a generally serpentine configuration.

6. The device of claim 1, wherein the barrel has an inner diameter and the tortuous groove has a length at least 5 times greater than the inner diameter.

7. The device of claim 1, wherein the barrel has an inner diameter and the tortuous groove has a length at least 20 times greater than the inner diameter.

8. The device of claim 1, wherein the tortuous groove is a helical groove.

9. The device of claim 8, wherein the helical groove has a pitch ranging from 4 to 40 turns per centimeter.

10. The device of claim 1, wherein the piston includes a generally conical tip that extends outwardly into the chamber.

11. The device of claim 1, wherein the plurality of grooves communicate with the chamber at respective locations that are evenly spaced apart from each other along the inner surface of the barrel.

12. The device of claim 1, wherein the plurality of grooves have a generally trapezoidal cross-section.

13. The device of claim 12, wherein the plurality of grooves has a cross-sectional area ranging from 0.006 square millimeters to 0.06 square millimeters.

14. A method of assembling a dispensing device comprising:
providing a hollow barrel having two open ends and at least partially filled with a composition;
inserting a piston into one end of the barrel, the piston having two or more grooved regions, each of the two or more grooved regions having at least two tortuous grooves located on a surface of the piston and extending along an inner surface of the barrel to vent air pockets in and around the composition as the piston is inserted; and
advancing the piston further into the barrel to urge some of the composition toward an opposite end of the barrel while simultaneously urging some of the composition into and along the at least two tortuous grooves of the two or more grooved regions, wherein the at least two tortuous grooves of each of the two or more grooved regions maintains open communication between the composition and the one end as the piston traverses the barrel.

15. A method of dispensing a composition comprising:
providing a hollow barrel having two open ends and at least partially filled with the composition;
providing a piston received in one end of the barrel, the piston having two or more grooved regions, each of the two or more grooved regions having at least two tortuous grooves located on a surface of the piston and extending along an inner surface of the barrel; and
advancing the piston into the barrel to dispense the composition from an opposite end of the barrel while simultaneously urging the composition along the at least two tortuous grooves of the two or more grooved regions, wherein the at least two tortuous grooves of each of the two or more grooved regions maintains open communication between the composition and the one end as the piston traverses the barrel.

16. The method of claim 15, wherein the piston maintains a generally rigid shape and does not deflect or deform in response to a pressure differential between inside and outside of the barrel.

17. The method of claim 15, wherein the composition only travels along a portion of the at least two tortuous grooves of the two or more grooved regions when the piston is fully advanced into the barrel.

18. The method of claim 17, wherein the composition is a thixotropic or shear-thinning composition.

\* \* \* \* \*